US011762107B2

(12) United States Patent
Kok (10) Patent No.: US 11,762,107 B2
(45) Date of Patent: Sep. 19, 2023

(54) PROTECTION OF A GAMMA RADIATION DETECTOR WITH AN OPTICAL MODULATOR TO MODULATE AN AMOUNT OF TRANSMISSION BETWEEN A GAMMA SCINTILLATOR ARRAY AND A FIRST PHOTODETECTOR ARRAY (71) Applicant: KONINKLIJKE PHILIPS N.V., Eindhoven (NL)

(72) Inventor: Christiaan Kok, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/470,385

(22) PCT Filed: Dec. 21, 2017

(86) PCT No.: PCT/EP2017/084104
§ 371 (c)(1),
(2) Date: Jun. 17, 2019

(87) PCT Pub. No.: WO2018/115287
PCT Pub. Date: Jun. 28, 2018

(65) Prior Publication Data
US 2019/0310384 A1 Oct. 10, 2019

(30) Foreign Application Priority Data
Dec. 21, 2016 (EP) ..................................... 16205875

(51) Int. Cl.
*A61B 6/00* (2006.01)
*G01T 1/20* (2006.01)
(Continued)

(52) U.S. Cl.
CPC ............ *G01T 1/20181* (2020.05); *A61B 6/03* (2013.01); *A61B 6/032* (2013.01); *A61B 6/035* (2013.01);
(Continued)

(58) Field of Classification Search
CPC ........... A61B 6/03; A61B 6/032; A61B 6/035; A61B 6/037; A61B 6/42; A61B 6/4208;
(Continued)

(56) References Cited

U.S. PATENT DOCUMENTS 3,906,234 A 9/1975 Conrad
4,059,765 A 11/1977 Tatsuta
(Continued)

FOREIGN PATENT DOCUMENTS

EP 0287707 A2 10/1988
EP 2073039 A1 6/2009
(Continued)

OTHER PUBLICATIONS

International Search Report and Written Opinion for PCT/EP2017/084104, dated Apr. 5, 2018.

*Primary Examiner* — Allen C. Ho (57) ABSTRACT

The invention relates to a combined detector (660) comprising a gamma radiation detector (100) and an X-ray radiation detector (661). The gamma radiation detector (100) comprises a gamma scintillator array ($101_{x, y}$), an optical modulator (102) and a first photodetector array ($103_{a, b}$) for detecting the first scintillation light generated by the gamma scintillator array ($101_{x, y}$). The optical modulator (102) is disposed between the gamma scintillator array ($101_{x, y}$) and the first photodetector array ($103_{a, b}$) for modulating a transmission of the first scintillation light between the gamma scintillator array ($101_{x, y}$) and the first photodetector array ($103_{a, b}$). The optical modulator (102) comprises at
(Continued)

least one optical modulator pixel having a cross sectional area (102') in a plane that is perpendicular to the gamma radiation receiving direction (104). The cross sectional area of each optical modulator pixel (102') is greater than or equal to the cross sectional area of each photodetector pixel ($103'_{a,\,b}$).

16 Claims, 4 Drawing Sheets

(51) Int. Cl.
*G01T 1/24* (2006.01)
*G01T 1/164* (2006.01)
*G01T 1/161* (2006.01)
*G01T 1/16* (2006.01)
*A61B 6/03* (2006.01)

(52) U.S. Cl.
CPC ............... *A61B 6/037* (2013.01); *A61B 6/42* (2013.01); *A61B 6/4208* (2013.01); *A61B 6/4233* (2013.01); *A61B 6/4241* (2013.01); *A61B 6/4258* (2013.01); *A61B 6/4266* (2013.01); *A61B 6/44* (2013.01); *A61B 6/4429* (2013.01); *A61B 6/4435* (2013.01); *A61B 6/4441* (2013.01); *A61B 6/4447* (2013.01); *G01T 1/16* (2013.01); *G01T 1/161* (2013.01); *G01T 1/1603* (2013.01); *G01T 1/164* (2013.01); *G01T 1/1606* (2013.01); *G01T 1/1611* (2013.01); *G01T 1/1612* (2013.01); *G01T 1/1614* (2013.01); *G01T 1/1615* (2013.01); *G01T 1/1617* (2013.01); *G01T 1/1618* (2013.01); *G01T 1/20* (2013.01); *G01T 1/2002* (2013.01); *G01T 1/2006* (2013.01); *G01T 1/2008* (2013.01); *G01T 1/2018* (2013.01); *G01T 1/20183* (2020.05); *G01T 1/20185* (2020.05); *G01T 1/24* (2013.01); *G01T 1/243* (2013.01); *G01T 1/249* (2013.01)

(58) Field of Classification Search
CPC ... A61B 6/4233; A61B 6/4241; A61B 6/4258; A61B 6/4266; A61B 6/44; A61B 6/4429; A61B 6/4435; A61B 6/4441; A61B 6/4447; A61B 6/58; A61B 6/585; A61B 6/4275; A61B 6/4283; A61B 6/586; G01T 1/16; G01T 1/1603; G01T 1/1606; G01T 1/161; G01T 1/1611; G01T 1/1612; G01T 1/1614; G01T 1/1615; G01T 1/1617; G01T 1/1618; G01T 1/164; G01T 1/20; G01T 1/2002; G01T 1/2006; G01T 1/2008; G01T 1/2018; G01T 1/20181; G01T 1/20183; G01T 1/20185; G01T 1/24; G01T 1/249; G01T 1/242; G01T 1/166; G01T 1/20182; G01T 1/20186; G01T 1/20187; G01T 1/20188; G01T 1/243
USPC .................. 378/19, 98.8, 196–198, 5, 207; 250/370.09, 363.01, 363.02, 363.03, 250/363.04, 363.1
See application file for complete search history.

(56) References Cited

U.S. PATENT DOCUMENTS

| | | | |
|---|---|---|---|
| 5,461,232 A | 10/1995 | McCandless | |
| 5,693,947 A * | 12/1997 | Morton | G01T 1/185 250/370.09 |
| 6,215,843 B1 | 4/2001 | Saito | |
| 6,710,350 B2 * | 3/2004 | Ruzga | G01T 1/1642 250/366 |
| 8,111,447 B2 * | 2/2012 | Fairly | G02B 26/004 359/296 |
| 8,948,338 B2 * | 2/2015 | Barbato | G01T 1/2964 378/19 |
| 9,014,330 B2 * | 4/2015 | Takayama | A61B 6/54 250/363.04 |
| 9,035,261 B2 * | 5/2015 | Wang | G01T 1/2002 250/362 |
| 9,348,034 B2 * | 5/2016 | Tredwell | G01T 1/161 |
| 9,693,743 B2 * | 7/2017 | Arakita | A61B 6/4241 |
| 9,772,409 B2 * | 9/2017 | Granfors | G01T 1/2018 |
| 9,974,498 B2 * | 5/2018 | Humphrey | G01T 1/2006 |
| 10,197,511 B2 * | 2/2019 | Kato | G01N 23/046 |
| 10,231,678 B2 * | 3/2019 | Herrmann | A61B 6/032 |
| 10,247,832 B2 * | 4/2019 | Serafino | G01T 1/1615 |
| 10,371,830 B2 * | 8/2019 | Jacobs | G01T 1/2023 |
| 10,448,909 B2 * | 10/2019 | Wieczorek | A61B 6/5205 |
| 10,539,683 B2 * | 1/2020 | De Jong | G01T 1/1612 |
| 10,942,282 B2 * | 3/2021 | Wieczorek | A61B 6/4441 |
| 11,112,509 B2 * | 9/2021 | Jacobs | G01T 1/247 |
| 2009/0316253 A1 | 12/2009 | Fairley | |
| 2011/0170778 A1 | 7/2011 | Le Goaller | |
| 2013/0237818 A1 | 9/2013 | Herrmann | |
| 2014/0151562 A1 | 6/2014 | Wang | |
| 2016/0187499 A1 | 6/2016 | Granfors | |

FOREIGN PATENT DOCUMENTS

| | | |
|---|---|---|
| EP | 2482101 A1 | 8/2012 |
| JP | 2003098262 A | 4/2003 |
| WO | 2007043868 A2 | 4/2007 |
| WO | 2008065605 A1 | 6/2008 |
| WO | 2009141767 A1 | 11/2009 |

* cited by examiner

PROTECTION OF A GAMMA RADIATION DETECTOR WITH AN OPTICAL MODULATOR TO MODULATE AN AMOUNT OF TRANSMISSION BETWEEN A GAMMA SCINTILLATOR ARRAY AND A FIRST PHOTODETECTOR ARRAY

CROSS-REFERENCE TO PRIOR APPLICATIONS

This application is the U.S. National Phase application under 35 U.S.C. § 371 of International Application No. PCT/EP2017/084104, filed on Dec. 21, 2017, which claims the benefit of European Patent Application No. 16205875.4, filed on Dec. 21, 2016. These applications are hereby incorporated by reference herein.

FIELD OF THE INVENTION

The invention relates to a gamma radiation detector. The gamma radiation detector finds application in the gamma radiation detection field in general. Application areas such as medical imaging, materials inspection, security, and baggage handling are contemplated. In the medical imaging field the gamma radiation detector may for example be used to generate a gamma scintigraphy image or a Single Photon Emission Computed Tomography, i.e. a SPECT, image. The gamma radiation detector may also be used in combination with an X-ray detector that generates an X-ray image during an X-ray imaging or a Computed Tomography, i.e. a CT, imaging procedure.

BACKGROUND OF THE INVENTION

Gamma radiation detectors are used in various fields to generate an image corresponding to the distribution of a radioactive source. For example, in the nuclear medicine field the functioning of various organs is studied by measuring the distribution of a radiotracer in the body. The radiotracer is typically a gamma emitter that is injected into the patient by a physician. The radiotracer has an affinity with various biological molecules and processes which results in the radiotracer being preferentially absorbed in certain regions of interest within the body. After a predetermined uptake time, these regions of interest are monitored or imaged using one or more gamma detectors that detect gamma quanta emitted by the radiotracer during its radioactive decay.

One group of radiation detectors that are used in the detection of gamma quanta employ a scintillator element and an associated photodetector. Such detectors are termed "scintillation detectors" and operate in the following way: a gamma quant that is received by the scintillator element generates a scintillation light pulse in the scintillator element. The photodetector detects the scintillation light pulse and generates an electrical signal therefrom. Electronic processing may subsequently be used to analyze the generated electrical signals in order to confirm their authenticity; for example by analyzing their individual signal strength to determine the amount of scintillation light and thus the energy of the quant that caused it. This may be used to confirm that the electrical signal originated from a gamma quant, or to otherwise reject it as having originated from a quant having a different energy, or as having originated from a scattered gamma quant, or noise.

Such gamma scintillation detectors may suffer from a number of drawbacks. One issue is that of selectivity. Whilst the scintillator elements of such detectors are typically optimized for a particular gamma quant energy range, they typically also respond to quanta from a different energy range, such as X-ray radiation. Gamma radiation detectors are frequently operated in the vicinity of X-ray sources such as those used in X-ray or CT imaging systems. These may for example be used in an imaging procedure that combines X-ray or CT imaging with gamma scintigraphy or SPECT imaging. Stray X-ray radiation from the X-ray source may be absorbed by the scintillator element of the gamma radiation detector where it generates undesired scintillation light. The stray X-ray radiation may reach the scintillator element of the gamma radiation detector directly from the X-ray source, or after being scattered. In order to prevent such interference, such X-ray and gamma imaging systems are typically operated sequentially in time, i.e. intermittently. Moreover, a delay is typically required between the termination of the X-ray pulse and the start of gamma imaging data generation in order to allow this unwanted scintillation light in the gamma radiation detector to decay. This delay lengthens such an intermittent imaging procedure. In extreme cases the unwanted scintillation light signal from the X-ray source may cause the gamma photodetectors and/or associated electronics to saturate. Such "blinding" of the gamma radiation detector typically necessitates a longer delay, i.e. a "saturation recovery time", between the termination of the X-ray pulse, and the start of gamma imaging data generation. This "saturation recovery time" can also lengthen such an intermittent imaging procedure. This "blinding" issue is particularly acute in so-called stacked detectors in which an X-ray imaging detector is disposed in front of a gamma imaging detector to provide co-registered X-ray and gamma, i.e. nuclear, images. In such a stacked detector a significant proportion of X-ray quanta may pass through the X-ray detector without being absorbed and thus cause the electronic circuitry associated with the gamma radiation detector to saturate.

Document EP2482101A1 discloses a focused pinhole gamma detection device. A collimator is provided between the detector and the object space. The detection device further includes a pinhole shutter device with a control unit that is arranged to selectively switch a transmission state of at least one pinhole of at least one pinhole system between an open state and a closed state under the control of the control unit.

Document U.S. Pat. No. 6,215,843 discloses an X-ray CT scanner for producing a CT image of a subject by scanning an X-ray fan beam radiated by an X-ray source through the subject in a predetermined slice-thickness direction. The plurality of slices in the image have unequal segment pitches. The scanner further has a group of switches for selecting and combining the X-ray transmission data of the plurality of slices.

The invention seeks to address the above and other drawbacks of gamma radiation detectors.

SUMMARY OF THE INVENTION

The present invention seeks to provide a gamma radiation detector having reduced susceptibility to stray radiation, particularly X-ray radiation. Further advantages from the described invention will also be apparent to the skilled person. Thereto a gamma radiation detector, a combined detector, an imaging arrangement, an imaging configuration and a computer program product are provided. Various advantageous methods are also defined by the independent claims.

The gamma radiation detector includes a gamma scintillator array comprising a plurality of first scintillator elements for generating first scintillation light in response to received gamma quanta; an optical modulator; and a first photodetector array for detecting the first scintillation light generated by the gamma scintillator array. The gamma scintillator array, the optical modulator and the first photodetector array are arranged in a stacked configuration along a gamma radiation receiving direction. Moreover, the optical modulator is disposed between the gamma scintillator array and the first photodetector array for modulating a transmission of the first scintillation light between the gamma scintillator array and the first photodetector array. The optical modulator comprises at least one optical modulator pixel, and the optical modulator pixel has a cross sectional area in a plane that is perpendicular to the gamma radiation receiving direction. The first photodetector array comprises a plurality of photodetector pixels, and each photodetector pixel has a cross sectional area in said plane. Furthermore, the cross sectional area of each optical modulator pixel is greater than or equal to the cross sectional area of each photodetector pixel.

In so doing a gamma radiation detector is provided with an optical modulator, i.e. a shutter, between the gamma scintillator array and its associated first photodetector array. The optical modulator can thus be used to control the amount of scintillation light detected by the first photodetector array. The optical modulator may thus be used to optically switch-off the photodetector detector portion of the gamma scintillation detector. The optical modulator can thus, for example, be used to protect the first photodetector array from unwanted scintillation light caused by X-ray radiation falling on the gamma radiation detector and which might otherwise "blind" the photodetector, or saturate its associated electronic circuitry. Since only the optical scintillation light signal is modulated, this can be achieved quickly. This is in contrast to a known technique in which a pinhole collimator of a gamma radiation detector is blocked with a necessarily dense and heavy, gamma-absorbing shutter. Moreover, as described herein, the possibility to optically switch-off the scintillation light permits various dark-state signal measurements on the first photodetector array associated with the gamma radiation detector. In the inventive gamma radiation detector the cross sectional area of each optical modulator pixel is greater than or equal to the cross sectional area of each photodetector pixel. This provides modulation of the scintillation light falling on the entire photodetector pixel.

In accordance with one aspect a combined detector includes the inventive gamma radiation detector and an X-ray radiation detector. The X-ray radiation detector is disposed along the gamma radiation receiving direction and on the opposite side of the gamma scintillator array to the first photodetector array. X-ray quanta are detected by the X-ray radiation detector whereas higher energy gamma quanta pass through the X-ray radiation detector and are absorbed by the gamma radiation detector. This arrangement of the X-ray radiation detector with respect to the gamma radiation detector provides mutual registration of the images generated by each system. However it has the drawback that stray X-ray quanta that are not absorbed in the X-ray detector may be absorbed in the gamma scintillator array of the gamma radiation detector. In order to prevent interference between the X-ray source and the gamma radiation detector, this detector configuration is typically operated intermittently. In other words, gamma radiation detection is performed intermittently between bursts of X-ray radiation. Under some circumstances the stray X-ray radiation generates sufficient unwanted scintillation light on the first photodetector array of the gamma radiation detector to saturate its associated electronic circuitry. Typically the detection of gamma radiation must therefore be delayed for a "saturation recovery time" after the termination of the X-ray pulse in order to give the electronics associated with the first photodetector array sufficient time to recover. In the combined detector the optical modulator can be used to protect the first photodetector array of the gamma radiation detector from such unwanted scintillation light. The optical modulator can thus be used to prevent saturation of the electronics associated with the first photodetector array whilst the X-ray detector is detecting X-ray quanta. This in-turn obviates the need for a saturation recovery time and reduces the duration of such an intermittent imaging procedure.

In accordance with another aspect an imaging arrangement is provided. The imaging arrangement includes the combined detector, an X-ray source, and a control unit. The control unit is in communication with the X-ray source and the optical modulator and is configured to control the optical transmission of the optical modulator in synchronization with the emission of X-ray radiation from the X-ray source. As described above with reference to the combined detector, unwanted scintillation light in the gamma radiation detector that is generated by unabsorbed X-ray quanta can saturate the electronics associated with the first photodetector array. Unwanted scintillation light may likewise be generated from scattered X-ray quanta. Moreover, even if the unwanted scintillation light caused by the scattered X-rays is insufficient to saturate the electronics of the first photodetector array, the fact that it generates scintillation light alone typically requires that the detection of gamma radiation is delayed for at least the "decay time" of the scintillator elements in the gamma scintillator array after the X-ray pulse has terminated. This is because the unwanted scintillation light that is generated by the X-ray quanta in the gamma radiation detector would otherwise have a variable baseline. Thus, the use of the inventive gamma radiation detector in the imaging arrangement, and wherein the optical transmission of the optical modulator is controlled in synchronization with the emission of X-ray radiation from the X-ray source, allows for the use of a shorter interval between termination of the X-ray radiation pulse and the start of collection of gamma imaging data.

In accordance with another aspect an imaging configuration is provided. The imaging configuration includes the inventive gamma radiation detector, an X-ray source, an X-ray detector, and a control unit. The X-ray source and X-ray detector define a field of view and the gamma radiation detector is positioned relative to the X-ray detector for generating gamma image data from a region that at least partially overlaps with the field of view. The control unit is in communication with the X-ray source and the optical modulator and is configured to control the optical transmission of the optical modulator in synchronization with the emission of X-ray radiation from the X-ray source. The imaging configuration corresponds to the above-described imaging arrangement with the exception that the X-ray radiation detector is no longer necessarily disposed along the gamma radiation receiving direction of the gamma radiation detector. Since X-ray quanta from an X-ray source may be scattered in various directions, a similar risk that X-ray radiation interferes with gamma radiation detection exists in an imaging configuration in which the separate X-ray and gamma radiation detectors have overlapping fields of view or are used in close proximity to one another. This problem therefore may occur in combined gamma imaging—X-ray imaging arrangements in which the X-ray and gamma detectors are mounted separately about a patient to view a region of interest from different angles. The benefits that were described in relation to the imaging arrangement also apply to the imaging configuration. Indeed it has been found that significant scattered X-ray radiation may also affect the gamma radiation detector.

In accordance with another aspect a normalization method for determining electrical offset signals of the first photodetector array of the inventive gamma radiation detector is provided. The normalization method includes the steps of i) switching the optical modulator into a optically blocking state, such that the transmission of the first scintillation light between the gamma scintillator array and the first photodetector array is inhibited ii) and measuring, whilst the optical modulator is in the optical blocking state, electrical offset signals generated by the first photodetector array. In this aspect the optical modulator of the gamma radiation detector is used to perform a so-called "dark state" measurement. The dark-state electrical offset signals, which may be currents or voltages, act as a baseline to the electrical signals generated by the first photodetector array during the detection of gamma quanta. The normalization method generates normalization data that may be subtracted from corresponding electrical signal data generated during the detection of gamma radiation as part of an imaging method. The normalization method may be used to improve the image quality of subsequently reconstructed images. In another method described herein, the same normalization data may be used to identify faulty pixels in the photodetector array, for example by comparing each electrical offset signal with an expected offset signal range.

BRIEF DESCRIPTION OF THE FIGURES

FIG. 9 illustrates in FIG. 9A a waveform corresponding to X-ray emission, Xem, and in FIG. 9B a waveform corresponding to optical modulator transmission, OMTx, that may be used in accordance with the embodiment of FIG. 7.

DETAILED DESCRIPTION OF THE INVENTION

In order to illustrate the principles of the present invention a gamma radiation detector 100 is described with particular reference to the detection of gamma quanta in a gamma scintigraphy imaging system. It is however to be appreciated that the gamma radiation detector 100 also finds application in other medical imaging applications such as SPECT imaging. The gamma radiation detector 100 may also be used in conjunction with X-ray and X-ray computed tomography, i.e. CT imaging systems. Moreover the gamma radiation detector 100 may be used in non-imaging applications both in and beyond the medical field.

Figure 1A:
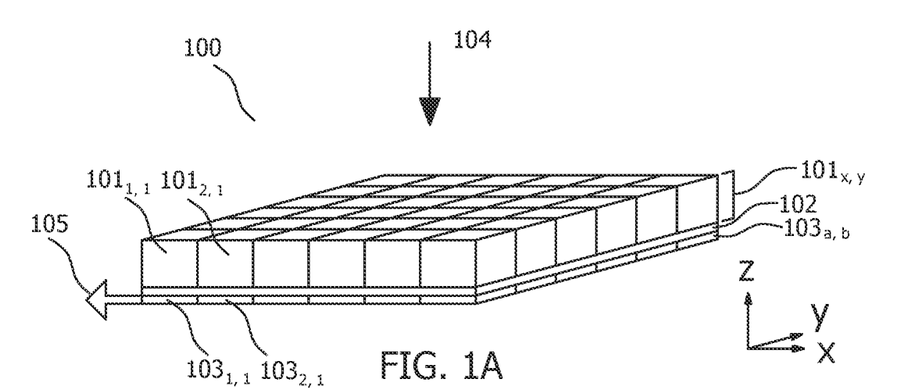
FIG. 1A illustrates a first embodiment of a gamma radiation detector 100 that includes gamma scintillator array 101$_{x, y}$, optical modulator 102, and first photodetector array 103$_{a, b}$.
Figure 1B:
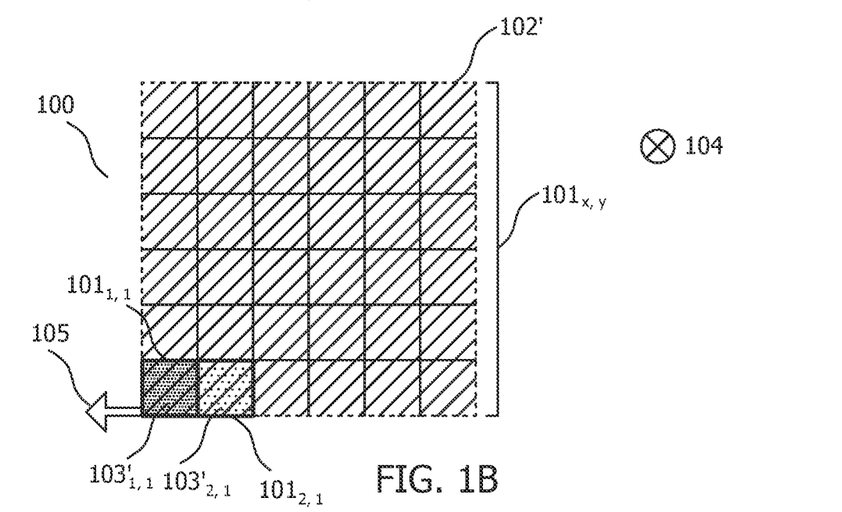
FIG. 1B illustrates the gamma radiation detector 100 of FIG. 1A as a plan view of the x-y plane, and in which the cross sectional area 102' of a pixel of optical modulator 102 is highlighted by the hatched region.

FIG. 1A illustrates a first embodiment of a gamma radiation detector 100 that includes gamma scintillator array 101$_{x, y}$, optical modulator 102, and first photodetector array 103$_{a, b}$. Corresponding FIG. 1B illustrates the gamma radiation detector 100 of FIG. 1A as a plan view of the x-y plane, and in which the cross sectional area 102' of a pixel of optical modulator 102 is highlighted by the hatched region. Gamma scintillator array 101$_{x, y}$ in FIG. 1A includes a plurality of first scintillator elements such as 101$_{1, 1}$ and 101$_{2, 1}$ that are suitable for generating scintillation light, termed herein "first scintillation light", in response to received gamma quanta. First photodetector array 103$_{a, b}$ is suitable for detecting the first scintillation light generated by the gamma scintillator array 101$_{x, y}$. As illustrated in FIG. 1A, gamma scintillator array 101$_{x, y}$, optical modulator 102 and first photodetector array 103$_{a, b}$ are arranged in a stacked configuration along gamma radiation receiving direction 104. Thus gamma radiation detector 100 is arranged for receiving gamma quanta along gamma radiation receiving direction 104. Moreover, optical modulator 102 is disposed between the gamma scintillator array 101$_{x, y}$ and first photodetector array 103$_{a, b}$ in order to modulate the transmission of the first scintillation light between the gamma scintillator array 101$_{x, y}$ and the first photodetector array 103$_{a, b}$. Optical modulator 102 includes at least one optical modulator pixel, and the optical modulator pixel has a cross sectional area 102', in a plane, that is perpendicular to the gamma radiation receiving direction 104. With reference to corresponding FIG. 1B the optical modulator pixel has a cross sectional area 102' in the x-y plane. First photodetector array 103$_{a, b}$ in FIG. 1A includes a plurality of photodetector pixels, e.g. 103$_{1, 1}$ and 103$_{2, 1}$, and each photodetector pixel has a cross sectional area 103'$_{a, b}$, e.g. dotted regions 103'$_{1,1}$ and 103'$_{2,1}$ in corresponding FIG. 1B, in the plane that is perpendicular to the gamma radiation receiving direction 104. Moreover, the cross sectional area 102' of each optical modulator pixel is greater than or equal to the cross sectional area 103'$_{a, b}$ of each photodetector pixel.

In operation, gamma radiation detector 100 in FIG. 1A may operate in the following manner: Gamma quanta received by gamma radiation detector 100 along gamma radiation receiving direction 104 are absorbed within one or more of scintillator elements of the gamma scintillator array. Each absorbed gamma quant generates a burst of scintillation light termed herein "first scintillation light". The first scintillation light is typically retained within the scintillation element in which it is generated by means of reflective layers not shown in FIG. 1A that are wrapped around all surfaces of each scintillator element except for the surface that faces first photodetector array $103_{a,\ b}$. Optical modulator 102 is switchable between at least a first transmission state and a second transmission state. When the optical modulator 102 is in the first transmission state the first scintillation light is transmitted by the optical modulator 102 to one or more corresponding pixels in first photodetector array $103_{a,\ b}$ where it is detected, resulting in electrical signals at first photodetector array electrical output bus 105. When the optical modulator 102 is in the second transmission state, the second transmission state having an optical transmission to first scintillation light that is lower than the first transmission state, a reduced amount of first scintillation light is transmitted by the optical modulator 102 to the one or more corresponding pixels in first photodetector array $103_{a,\ b}$. The first transmission state may be greater than 90%, greater than 80%, greater than 70%, greater than 60%, greater than 50%, greater than 40%, greater than 30%, greater than 20%, or greater than 10%, and the second transmission state may be less than said values. In one example the first transmission state is greater than 90% and the second transmission state is less than 10%. In another example the first transmission state is greater than 90% and the second transmission state is less than 1%. The second transmission state may represent an absorbing state wherein an undetectable amount of first scintillation light is transmitted by optical modulator 102. Optical modulator 102 is thus arranged to modulate the transmission of first scintillation light between the scintillator element in which it was generated, and the one or more corresponding pixels in first photodetector array $103_{a,\ b}$. In so doing gamma radiation detector 100 is provided with an optical modulator 102, i.e. a shutter, between gamma scintillator array $101_{x,\ y}$ and its associated first photodetector array $103_{a,\ b}$. Optical modulator 102 can thus be used to control the amount of first scintillation light that is detected by first photodetector array $103_{a,\ b}$. The optical modulator 102 may thus be used to optically control, or even optically switch-off, first photodetector array $103_{a,\ b}$. Optical modulator 102 can thus, for example, be used to protect first photodetector array $103_{a,\ b}$ from unwanted scintillation light caused by stray X-ray radiation falling on gamma radiation detector 100 and which might otherwise "blind" first photodetector array $103_{a,\ b}$, or even saturate its associated electronic circuitry. Since the first scintillation light is modulated in gamma radiation detector 100, this can be achieved quickly. This is in contrast to a known technique in which a pinhole collimator of a gamma radiation detector 100 is blocked with a necessarily dense and heavy, gamma-absorbing shutter. Since the cross sectional area 102' of each optical modulator pixel is greater than or equal to the cross sectional area $103'_{a,\ b}$ of each photodetector pixel. modulation of the scintillation light falling on the entire photodetector pixel is achieved.

The materials used for the scintillator elements in gamma scintillator array $101_{x,\ y}$ in FIG. 1A may be selected from a wide range of compositions including Lutetium-yttrium oxyorthosilicate, i.e. LYSO, $LaBr_3$, $CaGa_2S_4$, $SrGa_2S_4$, $BaGa_2S_4$, CaS, SrS, NaI and the broad group of materials known as garnets. Crystalline, polycrystalline and ceramic forms thereof are contemplated.

Optical modulator 102 in FIG. 1A may employ one or more of the following optical effects to modulate the transmission of the first scintillation light between the gamma scintillator array $101_{x,\ y}$ and the first photodetector array $103_a$, i) the absorption ii) the reflection and iii) the scattering, of the first scintillation light. In a preferred example, absorption of first scintillation light is preferred. Moreover, a combination of these optical effects may be used. Moreover, optical modulator 102 may include for example i) a liquid crystal device ii) an electrochromic device a MEMS device iv) an electrowetting device v) an electrophoretic device. Preferably a liquid crystal device is used.

First photodetector array $103_{a,\ b}$ in FIG. 1A may for example include an array of photodetectors such as photodiodes. Preferably an array of silicon photomultiplier, i.e. SiPM, photodiodes is used, such as a Philips Digital Photon Counting, PDPC, SiPM photodetector array. Alternatively first photodetector array $103_a$, may include an array of photomultiplier tubes, position sensitive photodetectors, and so forth.

Figure 1C:
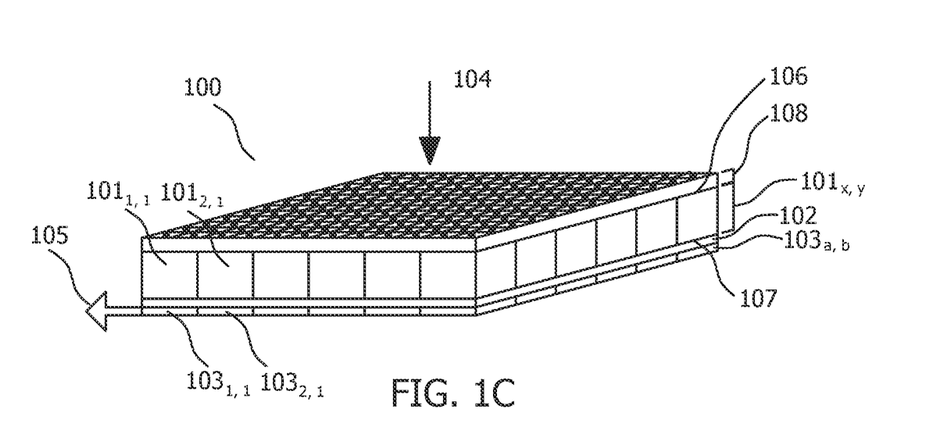
FIG. 1C illustrates the gamma radiation detector 100 of FIG. 1A together with gamma radiation collimator 108.

FIG. 1C illustrates the gamma radiation detector 100 of FIG. 1A together with gamma radiation collimator 108. Gamma scintillator array $101_y$ in FIG. 1C corresponds to gamma scintillator array $101_{x,\ y}$ in FIG. 1A, and further illustrates gamma radiation receiving face 106 and opposing scintillation light output face 107. Scintillation light output face 107 is arranged to face optical modulator 102. Moreover gamma radiation detector 100 in FIG. 1C includes gamma radiation collimator 108 which is suitable for collimating gamma quanta. Gamma radiation receiving face 106 of gamma scintillator array $101_{x,\ y}$ is arranged to face gamma radiation collimator 108. Gamma radiation collimator 108 may for example be a pinhole collimator, or formed from a 1D or a 2D array of septa configured to collimate gamma quanta. Gamma radiation collimator 108 may include one or multiple pinholes/septa per scintillator element. Gamma radiation collimator 108 may be formed from a dense metal such as lead or tungsten or gold.

In FIG. 1 the cross sectional area 102' of each scintillator element of the gamma scintillator array $101_{x,\ y}$ in a plane that is perpendicular to the gamma radiation receiving direction 104 was illustrated as being equal to the cross sectional area $103'_{a,\ b}$ of each photodetector pixel, however other arrangements are also suitable, for example the cross sectional area 102' of each scintillator element of the gamma scintillator array $101_{x,\ y}$ may alternatively be less than, or even greater than the cross sectional area $103'_{a,\ b}$ of each photodetector pixel. Moreover the cross sectional area 102' of optical modulator 102, i.e. 102', in a plane that is perpendicular to the gamma radiation receiving direction 104, was illustrated as being greater than the cross sectional area $103'_{a,\ b}$ of each photodetector pixel.

Figure 2A:
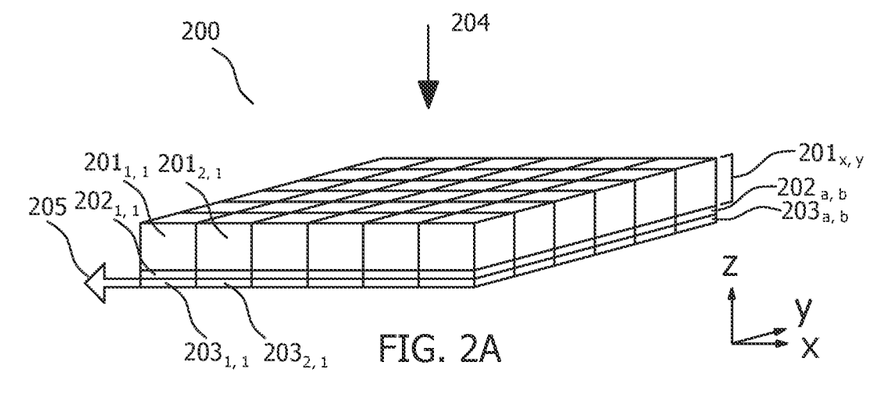
FIG. 2A illustrates a second embodiment of a gamma radiation detector 200 that includes gamma scintillator array 201$_{x, y}$, optical modulator 202$_{a, b}$, and first photodetector array 203$_{a, b}$.
Figure 2B:
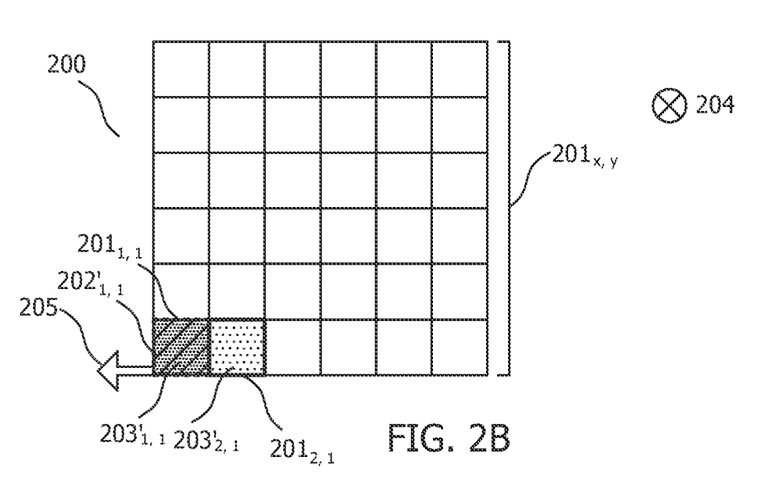
FIG. 2B illustrates the gamma radiation detector 200 of FIG. 2A as a plan view of the x-y plane, and in which the cross sectional area 202'$_{a, b}$ of a pixel of optical modulator 202 is highlighted by the hatched region.
Figure 2C:
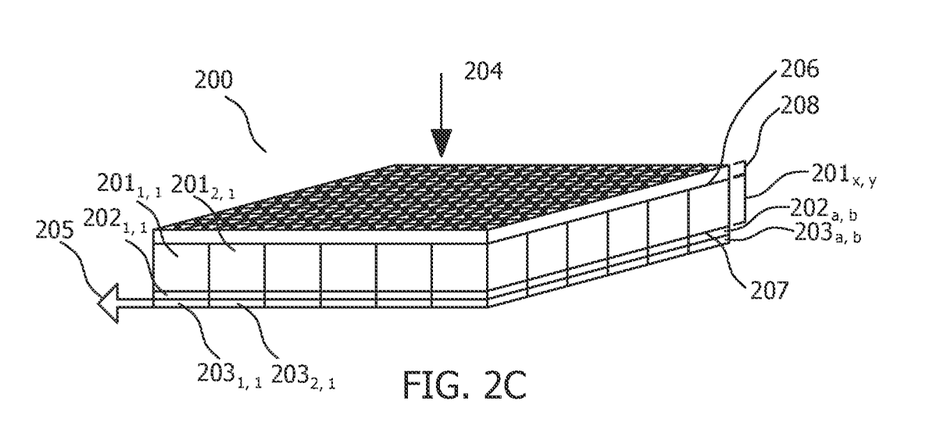
FIG. 2C illustrates the gamma radiation detector 200 of FIG. 2A together with gamma radiation collimator 208.

FIG. 2A illustrates a second embodiment of a gamma radiation detector 200 that includes gamma scintillator array $201_{x,\ y}$, optical modulator $202_{a,\ b}$, and first photodetector array $203_{a,\ b}$. Corresponding FIG. 2B illustrates the gamma radiation detector 200 of FIG. 2A as a plan view of the x-y plane, and in which the cross sectional area $202'_{a,\ b}$ of a pixel of optical modulator 202 is highlighted by the hatched region. FIG. 2C illustrates the gamma radiation detector 200 of FIG. 2A together with gamma radiation collimator 208. The gamma radiation detector 200 of FIG. 2 therefore corresponds to that of FIG. 1 except that in FIG. 2 the cross sectional area $202'_{a,\ b}$ of each pixel of optical modulator $202_{a,b}$ in a plane that is perpendicular to the gamma radiation receiving direction 204, is equal to the cross sectional area 102' of each photodetector pixel $203'_{a,b}$. Gamma radiation detector 200 in FIG. 2 otherwise operates in the same way as that in FIG. 1 to generate electrical signals at first photodetector array electrical output bus 205. Again, since the cross sectional area $202'_{a,b}$ of each optical modulator pixel is equal to the cross sectional area of each photodetector pixel $203'_{a,b}$, modulation of the scintillation light falling on the entire photodetector pixel $203'_{a,b}$ is achieved. Alternative arrangements which preserve the criteria that the cross sectional area 102' of each optical modulator pixel is greater than or equal to the cross sectional area of each photodetector pixel $103'_{a,b}$ are also possible, such as each optical modulator pixel having a cross sectional area 102' that is a non-integral multiple of the cross sectional area 102' of each photodetector pixel, and moreover the array of optical modulator pixels may be offset from the array of photodetector pixels.

Moreover, an optical mask, termed a "black mask" in the display field, may additionally be disposed between the optical modulator 102, $202_{a,b}$, of FIG. 1 and FIG. 2. and the first photodetector array $103_{a,b}$, $203_{a,b}$ or between optical modulator 102, $202_{a,b}$ and gamma scintillator array $101_{x,y}$, $201_{x,y}$ in order to provide complete modulation by the optical modulator of the first scintillation light falling on the photodetector pixels. Such a black mask may be formed from an optically absorbing polymer, or by a metal and so forth.

Figure 3:
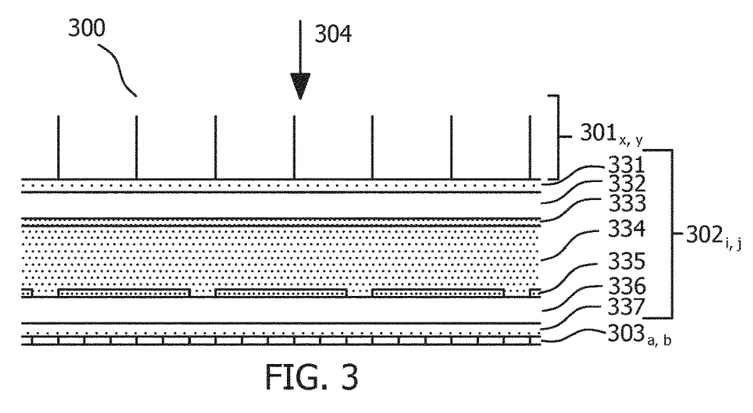
FIG. 3 illustrates third embodiment of a gamma radiation detector 300 in which an optical modulator is provided by a passive matrix liquid crystal array that includes a plurality of optical modulator pixels 302$_{i, j}$.

FIG. 3 illustrates third embodiment of a gamma radiation detector 300 in which an optical modulator is provided by a passive matrix liquid crystal array that includes a plurality of optical modulator pixels $302_{i,j}$. The Figure shows a cross section of the x-y plane illustrated in FIG. 1A. As mentioned above, in a preferred example the optical modulation is provided by a liquid crystal device. A liquid crystal device is preferred owing to the fast switching speeds available, high on-state transmission, and mature status of the technology. In FIG. 3 an array of optical modulator pixels $302_{i,j}$ is disposed between gamma scintillator array $301_{x,y}$ and the first photodetector array $303_{a,b}$ in order to modulate a transmission of the first scintillation light between the gamma scintillator array $301_{x,y}$ and the first photodetector array $303_{a,b}$. The array of optical modulator pixels $302_{i,j}$ may include a liquid crystal layer 334 disposed between glass plates 332, 336. Crossed polarizer layers disposed on either side of the liquid crystal layer 334 are illustrated as layers 331, 337. Additional alignment layers not shown in FIG. 3 may also be used to build-in a polarization to the liquid crystal to program the orientation of the liquid crystal molecules in order to set a predetermined polarization when no external voltage is applied. The transmission of the first scintillation light between the gamma scintillator array $301_{x,y}$ and the first photodetector array $303_{a,b}$ is achieved by applying external voltages between row electrode 333 and one or more of column electrodes 335. The voltages cause a rotation in the molecule of liquid crystal layer 334, which in combination with optical effect of layers 331, 337, results in a modulation of the first scintillation light along gamma radiation receiving direction 304, and consequently a modulation of the first scintillation light falling on the pixels of first photodetector array $303_a$, b.

Figure 4:
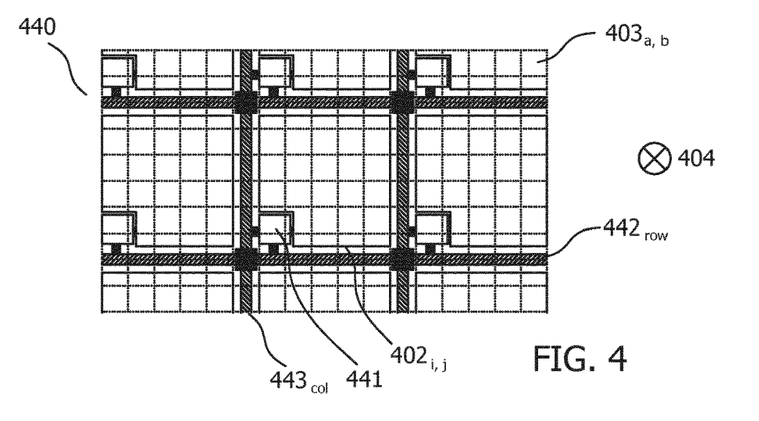
FIG. 4 illustrates an active matrix liquid crystal array 440.

FIG. 4 illustrates an active matrix liquid crystal array 440. The active matrix liquid crystal array 440 may be used in place of the passive matrix array of optical modulator pixels $302_{i,j}$ in FIG. 3; i.e. sandwiched between gamma scintillator array $301_{x,y}$ and the first photodetector array $303_{a,b}$. The Figure shows a plan view of the x-y plane illustrated in FIG. 1A. Thus gamma radiation receiving direction 404 is directed into the plane of the drawing and corresponds to gamma radiation receiving direction 104 in FIG. 1A. Active matrix devices have well-documented advantages over passive matrix devices, including improved control over the pixel cell transmission, the ability to provide a large area display effect, and the ability to provide optical corrections to individual pixels. Such an active matrix display device forms the basis of modern flat screen liquid crystal displays as used in televisions and mobile telephones and so forth. In FIG. 4 active matrix liquid crystal array 440 includes a plurality of optical modulator pixels $402_{i,j}$. Optical modulator pixels $402_{i,j}$ may be formed from an optically transparent conductor such as indium tin oxide, i.e. ITO. A transmission of the first scintillation light passing along gamma radiation receiving direction 404 between the gamma scintillator array, not shown in FIG. 4, and corresponding first photodetector array $403_{a,b}$ is achieved by setting voltages between the electrode of each optical modulator pixel $402_{i,j}$ and a transparent common electrode not shown in FIG. 4 and which is shared by all optical modulator pixels $402_{i,j}$. Thin film transistors, i.e. TFTs 441, electrically connected between a row address line $442_{row}$ and a column address line $442_{col}$ are used to set the voltage on the electrode of each optical modulator pixel $402_{i,j}$. The TFTs may for example be formed from amorphous silicon or from Indium Gallium Zinc Oxide, i.e. IGZO. A so-called "black mask" not shown in FIG. 4 which is known in the display field, may additionally be disposed between optical modulator comprising active matrix liquid crystal array 440 and the first photodetector array $303_{a,b}$ of FIG. 3, or between the optical modulator comprising active matrix liquid crystal array 440 and the gamma scintillator array $301_{x,y}$ of FIG. 3 in order to ensure complete modulation by the optical modulator of the first scintillation light falling on the photodetector pixels.

Figure 5:
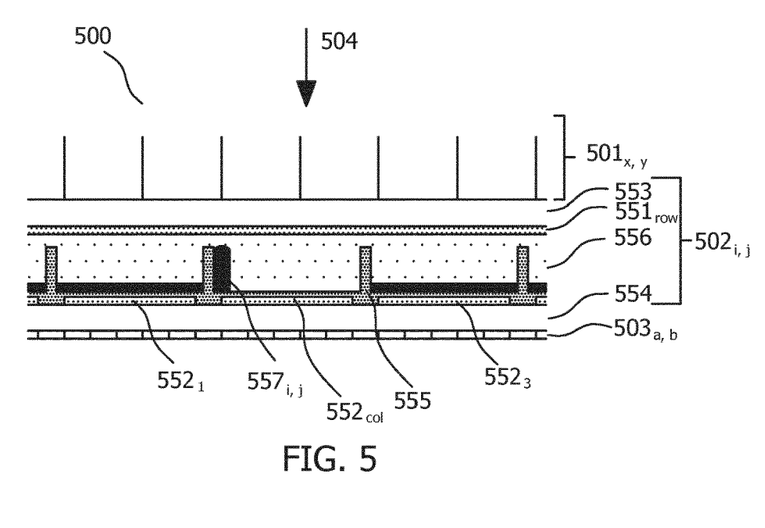
FIG. 5 illustrates a fourth embodiment of a gamma radiation detector 500 in which an optical modulator is provided by a passive matrix electrowetting array that includes a plurality of optical modulator pixels 502$_{i, j}$.

FIG. 5 illustrates a fourth embodiment of a gamma radiation detector 500 in which an optical modulator is provided by a passive matrix electrowetting array that includes a plurality of optical modulator pixels $502_{i,j}$. The Figure shows a cross section of the x-y plane; thus a cross section along gamma radiation receiving direction 504. The electrowetting effect, known from documents such as US20090316253A1, may thus be used to provide the desired optical modulation. In FIG. 5 passive electrowetting array comprising optical modulator pixels $502_{i,j}$ is disposed between gamma scintillator array $501_{x,y}$ and first photodetector array $503_{a,b}$ in order to modulate a transmission of the first scintillation light between the gamma scintillator array $501_{x,y}$ and the first photodetector array $503_{a,b}$. Passive matrix electrowetting array comprising optical modulator pixels $502_{i,j}$ may include a water-based conductive solution such as saline solution 556 disposed between glass plates 553, 554. The transmission of first scintillation light between gamma scintillator array $501_{x,y}$ and first photodetector array $503_{a,b}$ is achieved by applying external voltages between row electrode $551_{row}$ and one or more of column electrodes $552_{col}$. In FIG. 5 each optical modulator pixel $502_{i,j}$ is defined by the walls of a hydrophobic layer 555 that also serves to electrically isolate column electrodes $552_{col}$ from saline solution 556. Each pixel cell may be square, rectangular, hexagonal and so forth. An oil layer $557_{i,j}$ is disposed in each optical modulator pixel cell; the oil including a pigment or a dye that renders the oil absorbing across the wavelength range of the first scintillation light. When no external voltage is applied the hydrophobic nature of hydrophobic layer 555 ensures that the oil spreads out uniformly across the base of the optical modulator pixel cell, as seen above column electrodes $552_1$ and $552_3$. In this state the optical modulator has a second transmission state to first scintillation light received from gamma scintillator array $501_{x,\,y}$. When an external voltage is applied between the column electrode and the row electrode in FIG. 5 the oil layer is forced to the cell walls as seen in the central portion of FIG. 5 above the optical modulator pixel cell marked $552_{col}$. In this state the optical modulator has a first transmission state to first scintillation light emitted by gamma scintillator array $501_{x,\,y}$; the first transmission state having a higher transmission of first scintillation light than the second transmission state. In this first transmission state a greater proportion of first scintillation light is detected by first photodetector array $503_{a,\,b}$. In so doing the external voltage can be used to modulate the transmission of passive matrix electrowetting array comprising optical modulator pixels $502_{i,\,j}$. Electrowetting array comprising optical modulator pixels $502_{i,\,j}$ of FIG. 5 may alternatively be implemented as an active matrix device using TFTs to set the voltages across each optical modulator pixel in the same manner as illustrated in FIG. 4.

Other optical modulation effects such as a MEMS optical modulator device, or an electrophoretic device known from documents such as WO2008/065605, either in passive matrix or active matrix form, may be used to modulate a transmission of first scintillation light between the gamma scintillator array and the first photodetector array in a similar manner.

Figure 6:
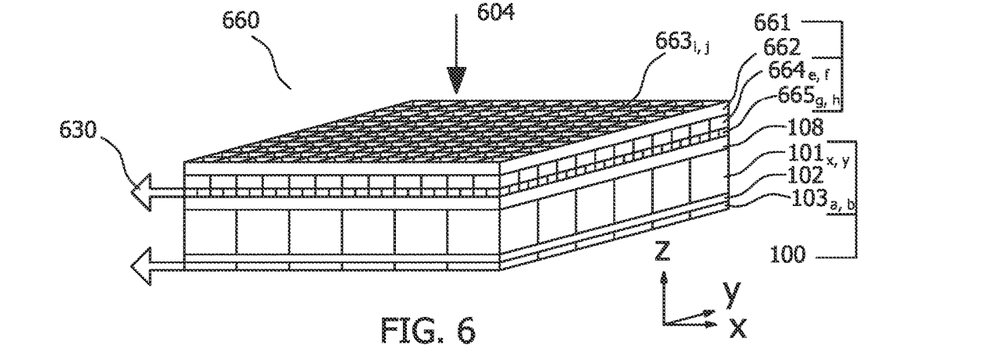
FIG. 6 illustrates a combined detector 660 that includes gamma radiation detector 100 and X-ray radiation detector 661.

As mentioned above, any of the gamma radiation detectors described above may be combined with an X-ray radiation detector. Thereto, FIG. 6 illustrates a combined detector 660 that includes gamma radiation detector 100 and X-ray radiation detector 661. The X-ray radiation detector 661 may be any conventional X-ray detector, for example a curved or planar X-ray imaging detector, or for example it may form part of a CT imaging detector. Moreover, the X-ray radiation detector 661 in FIG. 6 may include either an X-ray scintillator array or an array of direct conversion X-ray detector elements. The embodiment of FIG. 6 includes an X-ray scintillator array comprising a plurality of second scintillator elements $664_{e,\,f}$ for generating scintillation light, termed herein "second scintillation light" in response to received X-ray quanta. Moreover, X-ray radiation detector 661 is disposed along the gamma radiation receiving direction 604 and on the opposite side of the gamma scintillator array $101_{x,\,y}$ to first photodetector array $103_{a,\,b}$. The embodiment of FIG. 6 also includes a second photodetector array $665_{g,\,h}$ for detecting the second scintillation light. The second photodetector array $665_{g,\,h}$ is in optical communication with the second scintillator elements $664_{e,\,f}$ of the X-ray scintillator array in order to detect the second scintillation light. Furthermore, the X-ray scintillator array and the second photodetector array $665_{g,\,h}$ are arranged in a stacked configuration along the gamma radiation receiving direction 604. Examples of suitable X-ray scintillator materials for second scintillator elements $664_{e,\,f}$ include CsI, $Gd_2O_2S$, $Bi_4Ge_3O_{12}$ and the broad group of materials known as garnets. If, alternatively, an array of direct conversion X-ray detector elements is used, the array of direct conversion X-ray detector elements may be likewise arranged in a stacked configuration along the gamma radiation receiving direction 604. Examples of suitable direct conversion X-ray detector elements include Cadmium Zinc Telluride, i.e. CZT, or CdTe. Moreover, as illustrated in FIG. 6, X-ray radiation detector 661 may also include x-ray anti-scatter grid 662 that includes multiple apertures $663_{i,\,j}$.

In operation the embodiment of FIG. 6 operates in the following manner: X-ray quanta are received along gamma radiation receiving direction 604 and absorbed in second scintillator elements $664_{e,\,f}$ where they generate second scintillation light that is detected by corresponding second photodetector array $665_{g,\,h}$. This results in electrical signals at second photodetector array electrical output bus 630. The thickness and density of second scintillator elements $664_{e,\,f}$ is selected such that X-ray quanta are predominantly absorbed by the second scintillator elements, although as described above, some may reach gamma scintillator array $101_{x,\,y}$ of gamma radiation detector 100. Gamma radiation detector 100 operates in the same manner as described above for gamma quanta that are received along gamma radiation receiving direction 604, and these suffer little or negligibly from attenuation by X-ray radiation detector 661. As described above, optical modulator 102 can thus be used to optically switch-off first photodetector array $103_{a,\,b}$ by reducing its optical transmission of second scintillation light from a first, relatively higher level to a second relatively lower level. As described below, this switching may be performed in synchronization with the emission of X-ray radiation from an associated X-ray source, or alternatively in synchronization with X-ray quanta that are detected by X-ray radiation detector 661, i.e. based on electrical signals at second photodetector array electrical output bus 630.

Figure 7:
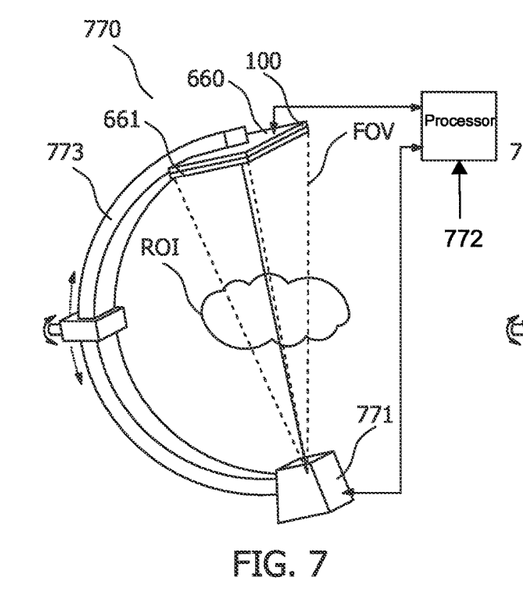
FIG. 7 illustrates an imaging arrangement 770 that includes combined detector 660 of FIG. 6, X-ray source 771 and processor 772.

FIG. 7 illustrates an imaging arrangement 770 that includes combined detector 660 of FIG. 6, X-ray source 771 and processor 772. X-ray source 771 and combined detector 660 are mounted on C-arm 773 for imaging a region of interest ROI within field of view FOV. Processor 772 is in communication with the X-ray source 771 and the optical modulator 102 of gamma radiation detector 100 and is configured to control the optical transmission of optical modulator 102 in synchronization with the emission of X-ray radiation from the X-ray source 771. In one example, processor 772 may be configured to control the emission of X-ray radiation from X-ray source 771. In another example, processor 772 may be configured to receive data from X-ray source 771 indicative of X-ray emission and control optical modulator 102 in accordance therewith. Processor 772 may be a known processor or implemented by dedicated electronic circuitry.

Figure 8:
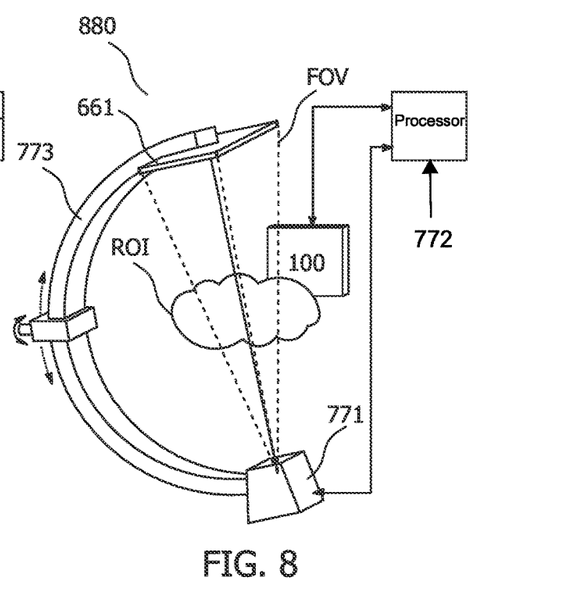
FIG. 8 illustrates an imaging configuration 880 that includes gamma radiation detector 100, X-ray source 771, X-ray detector 661 and processor 772.

FIG. 8 illustrates an imaging configuration 880 that includes gamma radiation detector 100, X-ray source 771, X-ray radiation detector 661 and processor 772. Imaging configuration 880 corresponds to imaging arrangement 770 with the exception that the X-ray radiation detector is no longer necessarily disposed along the gamma radiation receiving direction of the gamma radiation detector. In FIG. 8, X-ray source 771 and X-ray radiation detector 661 described above are exemplarily mounted to a C-arm. As with FIG. 7, other mounting configurations are also contemplated including mounting these to the gantry of a CT imaging system. Gamma radiation detector 100 in FIG. 8 is disposed relative to X-ray detector in order to generate gamma image data from a region, exemplified by region of interest ROI, that at least partially overlaps with field of view FOV defined by X-ray source 771 and X-ray radiation detector 661. Gamma radiation detector 100 in FIG. 8 may for example be mounted to a separate C-arm as C-arm 773 that supports x-ray source 771 and x-ray radiation detector 661, or be mounted to another support such as a robotic arm, or be mounted to a gantry such as a SPECT or gamma scintigraphy imaging gantry. The benefits that were described in relation to the imaging arrangement also apply to the imaging configuration. Indeed it has been found that significant scattered X-ray radiation may also affect the gamma radiation detector. Thereto imaging configuration 880 includes gamma radiation detector 100, X-ray source 771, X-ray radiation detector 661, and processor 772. X-ray source 771 and X-ray radiation detector 661 define a field of view FOV and gamma radiation detector 100 is positioned relative to X-ray radiation detector 661 for generating gamma image data from a region, such as region of interest ROI, that at least partially overlaps with field of view FOV. Processor 772 is in communication with X-ray source 771 and optical modulator 102 and is configured to control the optical transmission of optical modulator 102 in synchronization with the emission of X-ray radiation from X-ray source 771. Processor 772 in FIG. 8 may operate in the same manner as that described in relation to FIG. 7 in order to protect gamma radiation detector 100.

Figure 9A:
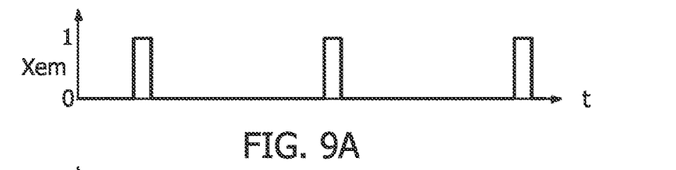
Figure 9B:
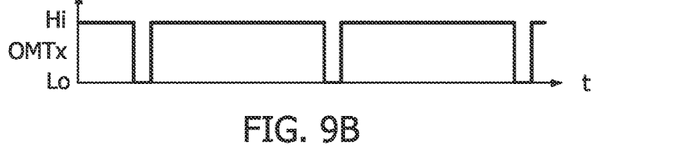

FIG. 9 illustrates in FIG. 9A a waveform corresponding to X-ray emission, Xem, and in FIG. 9B a waveform corresponding to optical modulator transmission, OMTx, that may be used in accordance with the embodiment of FIG. 7 or the embodiment of FIG. 8. In a preferred example mode of operation the synchronization described with reference to FIG. 7 comprises switching the optical modulator between a first transmission state and a second transmission state. The first transmission state, Hi, in FIG. 9B provides a higher transmission of first scintillation light than the second transmission state, Lo in FIG. 9B. As illustrated in corresponding FIG. 9A, optical modulator 102 is configured to have the second transmission state, i.e. OMTx=Lo, during a period when the X-ray source emits X-ray radiation, i.e. during the period when Xem=1. Optical modulator 102 is configured to have the first transmission state, OMTx=Hi, during a period when the X-ray source is not emitting X-ray radiation, i.e. during the period when Xem=0. In one example the period during which optical modulator 102 has the second transmission state, i.e. OMTx=Lo, exceeds the period during which X-ray source 771 emits X-ray radiation. Thus optical modulator 102 may remain in the second transmission state for a duration after X-ray source 771 stops emitting X-ray radiation. This additional duration may allow for any first scintillation light caused by afterglow of the gamma scintillator array scintillator to diminish. The additional duration may for example be 1%, or 5%, or 10%, or 20% or more of the period when the X-ray source emits X-ray radiation, i.e. of the period when Xem=1. A typical period for which Xem=1 is approximately 10 milliseconds and a typical period for which Xem=0 is approximately 300 milliseconds.

As described above, processor 772 in FIG. 7 or FIG. 8 may include a processor. The processor may execute the various method steps described above. Moreover, these method steps, or instructions may be stored on a computer program product. Thereto, a computer program product is disclosed. The computer program product comprises instructions which when executed by the processor cause the processor 772 of the imaging arrangement 770 or the processor 772 of the imaging configuration 880 to switch the optical modulator 102 between a first transmission state and a second transmission state. The first transmission state, i.e. OMTx=Hi, provides a higher transmission of first scintillation light than the second transmission state, i.e. OMTx=Lo. Moreover the optical modulator 102 has the second transmission state, i.e. OMTx=Lo, during a period when the X-ray source emits X-ray radiation.

In a further embodiment a normalization method for determining electrical offset signals of the first photodetector array of the gamma radiation detector 100 is disclosed. The normalization method includes the steps of:

switching the optical modulator 102 into an optically blocking state, such that the transmission of the first scintillation light between the gamma scintillator array 101$_{x,\,y}$ and the first photodetector array 103$_{a,\,b}$ is inhibited; and measuring, whilst the optical modulator 102 is in the optical blocking state, electrical offset signals generated by the first photodetector array 103$_{a,\,b}$.

In a further embodiment an imaging method is disclosed for use with gamma radiation detector 100. The imaging method include the steps of:

measuring, with the above normalization method, electrical offset signals generated by the first photodetector array 103$_{a,\,b}$ whilst the optical modulator 102 is in the optical blocking state;

switching the optical modulator 102 into an optically transmitting state, such that the transmission of the first scintillation light between the gamma scintillator array 101$_{x,\,y}$ and the first photodetector array 103$_{a,\,b}$ is higher than the transmission in the optical blocking state;

measuring electrical data signals generated by the first photodetector array 103$_{a,\,b}$ whilst the optical modulator 102 is in the optically transmitting state, the electrical data signals corresponding to a distribution of a radiotracer in a region of interest ROI;

subtracting the electrical offset signals from the corresponding electrical data signals to generate difference data electrical signals;

reconstructing a nuclear image corresponding to the distribution of the radiotracer in the region of interest ROI based on the difference data electrical signals.

In a further embodiment a method for identifying faulty pixels of the first photodetector array 103$_{a,\,b}$ of gamma radiation is disclosed. The presence of an electrical signal at first photodetector array electrical output bus 105 of first photodetector array 103$_{a,\,b}$ when the optical modulator is in the optically blocking state may be indicative of a faulty or so-called "hot" photodetector pixel. The method includes the steps of:

switching the optical modulator 102 into an optically blocking state, such that the transmission of the first scintillation light between the gamma scintillator array 101$_{x,\,y}$ and the first photodetector array 103$_{a,\,b}$ is inhibited;

measuring, whilst the optical modulator 102 is in the optical blocking state, electrical offset signals generated by the first photodetector array 103$_{a,\,b}$;

comparing each electrical offset signal with an expected offset signal range; and associating one or more photodetector pixels of the first photodetector array 103$_{a,\,b}$ that have an electrical offset signal that lies outside the predetermined range with a faulty status.

Moreover the above method steps, and/or other method steps disclosed herein, may be recorded in the form of instructions on computer-readable medium that is executable by a computer program product. The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk-read only memory "CD-ROM", compact disk-read/write "CD-R/W", Blu-Ray™ and DVD.

In summary, a gamma radiation detector has been described. The gamma radiation detector includes a gamma scintillator array comprising a plurality of first scintillator elements for generating first scintillation light in response to received gamma quanta; an optical modulator; and a first photodetector array for detecting the first scintillation light generated by the gamma scintillator array. Moreover, the optical modulator is disposed between the gamma scintillator array and the first photodetector array for modulating a transmission of the first scintillation light between the gamma scintillator array and the first photodetector array. The optical modulator comprises at least one optical modulator pixel, and the optical modulator pixel has a cross sectional area. The first photodetector array comprises a plurality of photodetector pixels, and each photodetector pixel has a cross sectional area. Furthermore, the cross sectional area of each optical modulator pixel is greater than or equal to the cross sectional area of each photodetector pixel. In so doing a gamma radiation detector is provided with an optical modulator that can be used to control the amount of scintillation light detected by the first photodetector array. The optical modulator may thus be used to optically switch-off the photodetector detector portion of the gamma scintillation detector.

The invention claimed is:
1. A combined detector, comprising:
an X-ray radiation detector; and
a gamma radiation detector comprising:
  a gamma scintillator array comprising a plurality of first scintillator elements for generating first scintillation light in response to received gamma quanta;
  an optical modulator; and
  a first photodetector array for detecting the first scintillation light generated by the gamma scintillator array;
  wherein the gamma scintillator array, the optical modulator, and the first photodetector array are arranged in a stacked configuration along a gamma radiation receiving direction;
  wherein the optical modulator is disposed between the gamma scintillator array and the first photodetector array for modulating a transmission of the first scintillation light between the gamma scintillator array and the first photodetector array;
  wherein the optical modulator comprises at least one optical modulator pixel, the at least one optical modulator pixel having a cross sectional area in a plane that is perpendicular to the gamma radiation receiving direction;
  wherein the first photodetector array comprises a plurality of photodetector pixels, each photodetector pixel of the plurality of photodetector pixels having a cross sectional area in the plane that is perpendicular to the gamma radiation receiving direction;
  wherein a cross sectional area of each optical modulator pixel of the at least one optical modulator pixel is greater than or equal to a cross sectional area of each photodetector pixel of the plurality of photodetector pixels; and
wherein the X-ray radiation detector is disposed along the gamma radiation receiving direction and on an opposite side of the gamma scintillator array to the first photodetector array.

2. The combined detector according to claim 1, wherein the gamma scintillator array comprises a gamma radiation receiving face and an opposing scintillation light output face;
  wherein the opposing scintillation light output face is arranged to face the optical modulator;
  wherein the gamma radiation detector further comprises a gamma radiation collimator for collimating gamma quanta; and
  wherein the gamma radiation receiving face is arranged to face the gamma radiation collimator.

3. The combined detector according to claim 1, wherein the optical modulator is configured to modulate a transmission of the first scintillation light between the gamma scintillator array and the first photodetector array by modulating at least one of i) an absorption, ii) a reflection, and iii) a scattering of the first scintillation light.

4. The combined detector according to claim 1, wherein the optical modulator comprises i) a liquid crystal device, ii) an electrochromic device, iii) a MEMS device, iv) an electrowetting device, or v) an electrophoretic device.

5. A computed tomography (CT) imaging detector comprising:
a combined detector, which comprises:
  an X-ray radiation detector, comprising: an X-ray anti-scatter grid disposed along a gamma radiation receiving direction, the X-ray radiation detector further comprising either: an X-ray scintillator array comprising a plurality of second scintillator elements for generating second scintillation light in response to received X-ray quanta: a second photodetector array for detecting the second scintillation light; wherein the second photodetector array is in optical communication with the plurality of second scintillator elements for detecting the second scintillation light; and wherein the X-ray scintillator array and the second photodetector array are arranged in a stacked configuration along the gamma radiation receiving direction; or an array of direct-conversion X-ray detector elements; wherein each direct-conversion X-ray detector element of the array of direct-conversion X-ray detector elements is configured to generate electrical signals in response to received X-ray quanta;
a gamma scintillator array comprising a plurality of first scintillator elements for generating first scintillation light in response to received gamma quanta;

an optical modulator; and a first photodetector array for detecting the first scintillation light generated by the gamma scintillator array;

wherein the gamma scintillator array, the optical modulator, and the first photodetector array are arranged in a stacked configuration along the gamma radiation receiving direction;

wherein the optical modulator is disposed between the gamma scintillator array and the first photodetector array for modulating a transmission of the first scintillation light between the gamma scintillator array and the first photodetector array;

wherein the optical modulator comprises at least one optical modulator pixel, the at least one optical modulator pixel having a cross sectional area in a plane that is perpendicular to the gamma radiation receiving direction;

wherein the first photodetector array comprises a plurality of photodetector pixels, each photodetector pixel of the plurality of photodetector pixels having a cross sectional area in the plane that is perpendicular to the gamma radiation receiving direction;

wherein a cross sectional area of each optical modulator pixel of the at least one optical modulator pixel is greater than or equal to a cross sectional area of each photodetector pixel of the plurality of photodetector pixels; and wherein the X-ray radiation detector is disposed along the gamma radiation receiving direction and on an opposite side of the gamma scintillator array to the first photodetector array.

6. An imaging arrangement comprising:

a combined detector, comprising: a gamma radiation detector, comprising:

a gamma scintillator array comprising a plurality of first scintillator elements for generating first scintillation light in response to received gamma quanta; an optical modulator; and a first photodetector array for detecting the first scintillation light generated by the gamma scintillator array;

wherein the gamma scintillator array, the optical modulator, and the first photodetector array are arranged in a stacked configuration along a gamma radiation receiving direction;

wherein the optical modulator is disposed between the gamma scintillator array and the first photodetector array for modulating a transmission of the first scintillation light between the gamma scintillator array and the first photodetector array;

wherein the optical modulator comprises at least one optical modulator pixel, the at least one optical modulator pixel having a cross sectional area in a plane that is perpendicular to the gamma radiation receiving direction;

wherein the first photodetector array comprises a plurality of photodetector pixels, each photodetector pixel of the plurality of photodetector pixels having a cross sectional area in the plane that is perpendicular to the gamma radiation receiving direction; and wherein a cross sectional area of each optical modulator pixel of the at least one optical modulator pixel is greater than or equal to a cross sectional area of each photodetector pixel of the plurality of photodetector pixels; and an X-ray radiation detector disposed along the gamma radiation receiving direction and on an opposite side of the gamma scintillator array to the first photodetector array; and an X-ray source; and a processor in communication with the X-ray source and the optical modulator, and is configured to control a transmission of the optical modulator in a synchronization with an emission of X-ray radiation from the X-ray source.

7. The imaging arrangement according to claim 6, wherein the processor is further configured to control the transmission of the optical modulator by switching the optical modulator between a first transmission state and a second transmission state;

wherein the first transmission state provides a higher transmission of the first scintillation light than the second transmission state; and wherein the optical modulator is configured to have the second transmission state during a period when the X-ray source emits X-ray radiation.

8. The imaging arrangement according to claim 6, wherein the optical modulator is configured to modulate the transmission of the first scintillation light between the gamma scintillator array and the first photodetector array by modulating at least one of i) an absorption, ii) a reflection, and iii) a scattering of the first scintillation light.

9. The imaging arrangement according to claim 6, wherein the optical modulator comprises i) a liquid crystal device, ii) an electrochromic device, iii) a MEMS device, iv) an electrowetting device, or v) an electrophoretic device.

10. The imaging arrangement according to claim 6, wherein the X-ray radiation detector comprises either:

an X-ray scintillator array comprising a plurality of second scintillator elements for generating second scintillation light in response to received X-ray quanta;

a second photodetector array for detecting the second scintillation light;

wherein the second photodetector array is in optical communication with the plurality of second scintillator elements for detecting the second scintillation light; and wherein the X-ray scintillator array and the second photodetector array are arranged in a stacked configuration along the gamma radiation receiving direction; or an array of direct-conversion X-ray detector elements; and wherein each direct-conversion X-ray detector element of the array of direct-conversion X-ray detector elements is configured to generate electrical signals in response to received X-ray quanta.

11. The imaging arrangement according to claim 10, wherein the X-ray radiation detector further comprises an X-ray anti-scatter grid; and wherein the X-ray anti-scatter grid is disposed along the gamma radiation receiving direction and on an opposite side of the X-ray scintillator array to the gamma radiation detector.

12. The imaging arrangement according to claim 6, wherein the gamma scintillator array comprises a gamma radiation receiving face and an opposing scintillation light output face;

wherein the opposing scintillation light output face is arranged to face the optical modulator;

wherein the gamma radiation detector further comprises a gamma radiation collimator for collimating gamma quanta; and wherein the gamma radiation receiving face is arranged to face the gamma radiation collimator.

13. A normalization method for determining electrical offset signals of the first photodetector array of the combined detector of claim 1, the normalization method comprising:
   switching the optical modulator into an optical blocking state, such that a transmission of the first scintillation light between the gamma scintillator array and the first photodetector array is inhibited; and
   measuring, whilst the optical modulator is in the optical blocking state, electrical offset signals generated by the first photodetector array.

14. An imaging method for use with the combined detector of claim 1, the imaging method comprising:
   measuring, with a normalization method for determining electrical offset signals generated by the first photodetector array whilst the optical modulator is in an optical blocking state;
   switching the optical modulator into an optically transmitting state, such that a transmission of the first scintillation light between the gamma scintillator array and the first photodetector array is higher than a transmission in the optical blocking state;
   measuring electrical data signals generated by the first photodetector array whilst the optical modulator is in the optically transmitting state, the electrical data signals corresponding to a distribution of a radiotracer in a region of interest;
   subtracting the electrical offset signals from a corresponding measured electrical data signals to generate difference data electrical signals; and
   reconstructing a nuclear image corresponding to the distribution of the radiotracer in the region of interest based on the difference data electrical signals.

15. A method of identifying faulty pixels of the first photodetector array of the combined detector of claim 1, the method comprising:
   switching the optical modulator into an optically blocking state, such that a transmission of the first scintillation light between the gamma scintillator array and the first photodetector array is inhibited;
   measuring, whilst the optical modulator is in the optical blocking state, electrical offset signals generated by the first photodetector array;
   comparing each electrical offset signal of the electrical offset signals with an expected offset signal range; and
   associating one or more photodetector pixels of the first photodetector array that have an electrical offset signal that lies outside a predetermined range with a faulty status.

16. A tangible, non-transitory computer readable medium that stores instructions, which, when executed by the processor of the imaging arrangement of claim 7, cause the processor of the imaging arrangement of claim 7 to switch the optical modulator between a first transmission state and a second transmission state; wherein:
   the first transmission state provides a higher transmission of the first scintillation light than the second transmission state; and
   the optical modulator has the second transmission state during a period when the X-ray source emits X-ray radiation.

* * * * *